(12) United States Patent (10) Patent No.: US 8,588,935 B2
Zimmerman (45) Date of Patent: Nov. 19, 2013

(54) IMPLANTABLE MEDICAL LEAD

(75) Inventor: James A. Zimmerman, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 125 days.

(21) Appl. No.: 13/079,870

(22) Filed: Apr. 5, 2011

(65) Prior Publication Data

US 2011/0257717 A1    Oct. 20, 2011

Related U.S. Application Data

(60) Provisional application No. 61/324,006, filed on Apr. 14, 2010.

(51) Int. Cl.
*A61N 1/00* (2006.01)

(52) U.S. Cl.
USPC ............................................. 607/116

(58) Field of Classification Search
USPC ............................................. 607/116
See application file for complete search history.

(56) References Cited

U.S. PATENT DOCUMENTS

| | | | |
|---|---|---|---|
| 6,002,956 A | 12/1999 | Schaer | |
| 6,233,488 B1 | 5/2001 | Hess | |
| 7,149,586 B2 | 12/2006 | Greenberg et al. | |
| 7,251,529 B2 | 7/2007 | Van Meerveld | |
| 2005/0246003 A1* | 11/2005 | Black et al. | 607/116 |
| 2006/0161219 A1 | 7/2006 | Mock et al. | |
| 2007/0255367 A1* | 11/2007 | Gerber et al. | 607/116 |
| 2008/0183263 A1* | 7/2008 | Alexander | 607/122 |
| 2008/0262582 A1 | 10/2008 | Alexander et al. | |
| 2009/0196471 A1* | 8/2009 | Goetz et al. | 382/128 |

\* cited by examiner

*Primary Examiner* — Robert N Wieland
(74) *Attorney, Agent, or Firm* — Mueting Raasch & Gebhardt PA

(57) ABSTRACT

An implantable medical lead includes a lead body, a first electrode, a second electrode, a third electrode, and a fourth electrode. The electrodes are located at fixed positions along the length of the lead body, and the second and third electrodes are positioned between the first and fourth electrodes. The first electrode has a proximal end, the fourth electrode has a distal end, and the distance from the proximal end of the first electrode to the distal end of the fourth electrode is between 5 centimeters and 7 centimeters. The combined length of the second and third electrodes is between 2.5 and 5 times greater than the combined length of the first and fourth electrodes. The lead may be used for applying electrical signals to an occipital nerve of a patient.

11 Claims, 5 Drawing Sheets

IMPLANTABLE MEDICAL LEAD

The present application claims priority to U.S. Provisional Patent Application No. 61/324,006, filed Apr. 14, 2010, which application is hereby incorporated by reference as if re-written in its entirety.

FIELD

The present disclosure relates generally to implantable medical leads; particularly to implantable medical leads configured to apply electrical signals to nerves.

BACKGROUND

Headaches, such as migraines, cluster headaches, and occipital neuralgia are often incapacitating and may lead to significant consumption of drugs to treat the symptoms. However, a rather large number of people are unresponsive to drug treatment, leaving them to wait out the episode or to resort to coping mechanisms. For refractive occipital neuralgia, nerve ablation or separation may effectively treat the pain.

Occipital nerve stimulation (ONS) may serve as an alternative for treatment of headache. ONS employs an electrical signal generator and a lead operably coupled to the signal generator and configured to deliver the signal to an occipital nerve. A distal portion of the lead is typically implanted in proximity to the occipital nerve such that one or more electrodes of the leads are in electrical communication with the occipital nerve. The proximal portions of the leads may then be connected to the signal generator such that electrical signals can be delivered from the signal generator to the electrodes to apply therapeutic signals to the occipital nerves.

The ability to properly locate the lead and select the proper electrodes of the lead for use in delivering the therapy can present problems or can be challenging. Given the anatomy of the occipital nerve and the configuration of most commercially available electrodes, in which all electrodes are of similar size and are spaced apart at regular intervals, it can be difficult to ensure that an electrical field generated using an electrode of the lead captures the intended nerve without a good deal of time and skill.

SUMMARY

This disclosure, among other things, describes a lead having electrodes sized and spaced in a manner to facilitate occipital nerve stimulation and implant procedures associated therewith.

In an embodiment, an implantable medical lead includes a lead body having a proximal portion and a distal portion and includes a plurality of contacts located at the proximal portion of the lead body for electrically coupling the lead with an electrical medical device. The lead further includes first, second, third and fourth electrodes located at the distal portion of the lead body for transmitting electrical signals to, or receiving electrical signals from, tissue of a patient. Each of the first, second, third and fourth electrode is electrically coupled with a discrete contact of the plurality of contacts. The second and third electrodes are positioned between the first and fourth electrodes. The first electrode has a proximal end, the fourth electrode has a distal end, and the distance from the proximal end of the first electrode to the distal end of the fourth electrode is between 5 centimeters and 7 centimeters. The combined length of the second and third electrodes is between 2.5 and 5 times greater than the combined length of the first and fourth electrodes. The size, spacing and configuration of electrodes of the lead are particularly well suited for occipital nerve stimulation, as will be described herein below in more detail.

One or more embodiments of the leads and methods described herein offer one or more advantages over current leads and methods, which advantages will be apparent to those of skilled in the art upon reading the following detailed description.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure.

Figure 1:
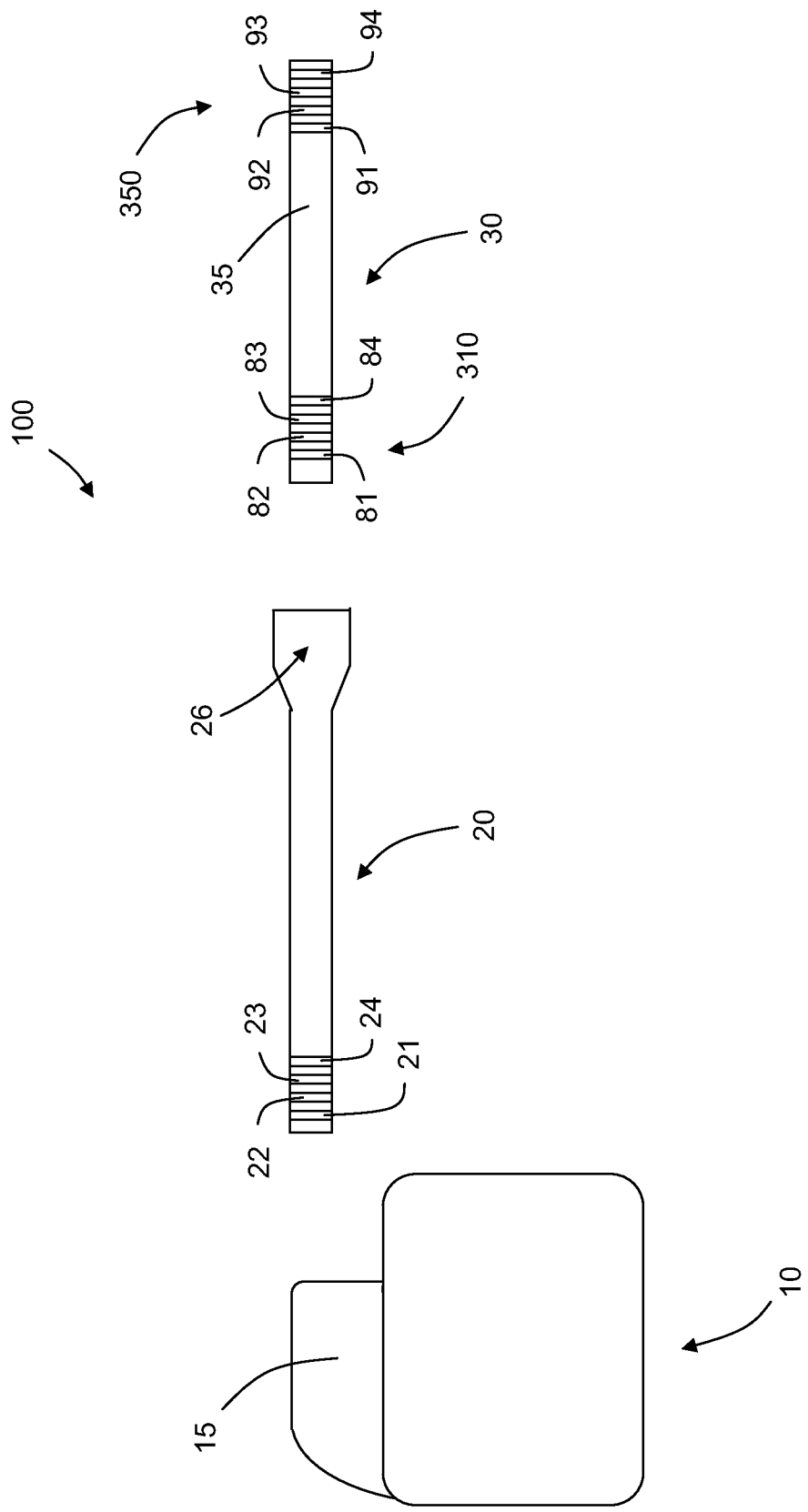
FIG. 1 is a schematic drawing illustrating an exemplary electrical signal generator system.

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to."

"Exemplary" or "representative" is used herein in the sense of "for example" or "for the purpose of illustration", and not in a limiting sense.

As used, herein, "providing" an article means making, using, purchasing, or otherwise obtaining the article.

As used herein, "implanted", "implantable" or the like with regard to a medical device, means that at least a portion of the device is placed or capable of being placed within a subject, such as a patient. That is, for the purpose of the present disclosure, a device is implanted whether it is fully implanted or partially implanted. For example, a lead may be considered implanted if a distal portion of the lead is placed at a target region in the patient while a proximal portion of the lead is located external to the patient.

This disclosure, among other things, relates to a lead having electrodes sized and spaced in a manner to facilitate occipital nerve stimulation and implant procedures associated therewith. Of course a lead described herein may be used for any suitable medical purpose including applying electrical signals to muscles, nerves other than an occipital nerve, or other tissues or for receiving electrical signals from tissue of a patient. Accordingly the leads described herein may be employed with nearly any electrical medical device or system. Representative examples of such medical devices include hearing implants, cochlear implants; sensing or monitoring devices; signal generators such as cardiac pacemakers or defibrillators, neurostimulators (such as spinal cord stimulators, brain or deep brain stimulators, peripheral nerve stimulators, vagal nerve stimulators, occipital nerve stimulators, subcutaneous stimulators, etc.), gastric stimulators; or the like. For purposes of occipital nerve stimulation, electrical signal generators such as Medtronic, Inc.'s Restore® or Synergy® series of implantable neurostimulators may be employed.

Referring to FIG. 1, a side view of an exemplary electrical signal generator system 100 is shown. In the depicted system 110, the electrical signal generator 10 includes a connector header 15 configured to receive a proximal portion of lead extension 20. The proximal portion of lead extension 20 contains a plurality of electrical contacts 21-24 that are electrically coupled to internal contacts (not shown) at distal connector 26 of lead extension 20. The connector header 15 of the signal generator 10 contains internal contacts (not shown) and is configured to receive the proximal portion of the lead extension 20 such that the internal contacts of the connector header 15 may be electrically coupled to the contacts 21-24 of the lead extension 20 when the lead extension 20 in inserted into the header 15.

The system depicted in FIG. 1 further includes a lead 30. The depicted lead 30 has a proximal portion 310 that includes a plurality of contacts 81-84 and a distal portion 350 that includes a plurality of electrodes 91-94. Each of the electrodes 91-94 may be electrically coupled to a discrete contact 81-84, e.g. via conductors (not shown) running through (e.g., within a lumen, embedded in the material of the body, or the like) the lead body 35. The distal connector 26 of the lead extension 20 is configured to receive the proximal portion 310 of the lead 30 such that the contacts 81-84 of the lead 30 may be electrically coupled to the internal contacts of the connector 26 of the extension 20. Accordingly, a signal generated by the signal generator 10 may be transmitted to a patient by an electrode 91-94 of lead 30 when lead is connected to extension 20 and extension 20 is connected to signal generator 10. It will be understood that lead 30 may be coupled to signal generator 10 without use of an extension 20. Any number of leads 30 or extensions 20 may be coupled to signal generator 10. Typically, one or two leads 30 or extensions 20 are coupled to signal generator 10.

Figure 2A:
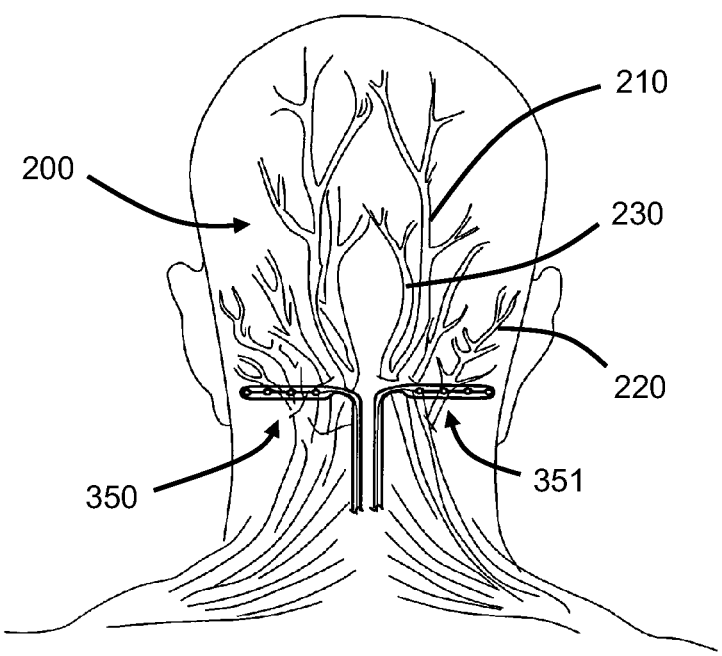
FIGS. 2A-B are schematic drawings of embodiments of distal portions of leads implanted in a patient and positioned for application of electrical signals to occipital nerves of a patient.
Figure 2B:
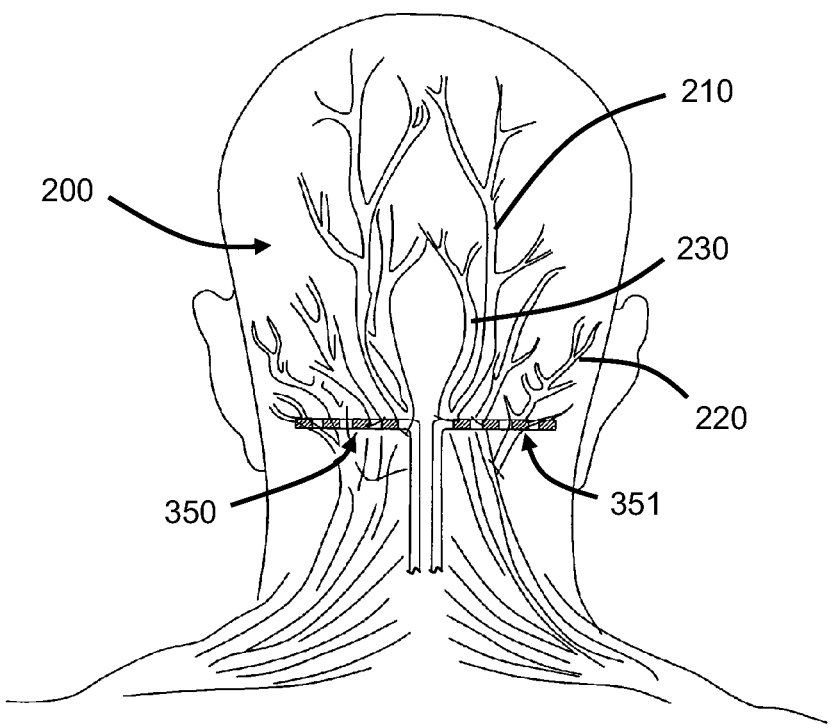

Referring now to FIGS. 2A-B, distal portions 350, 351 of leads are shown implanted in a subject to provide electrical signals to left and right occipital nerves 200. As used herein, occipital nerve 200 includes the greater occipital nerve 210, the lesser occipital nerve 220 and the third occipital nerve 230. The greater and lesser occipital nerves are spinal nerves arising between the second and third cervical vertebrae (not shown). The third occipital nerve arises between the third and fourth cervical vertebrae. The portion of the occipital nerve 200 to which an electrical signal is to be applied may vary depending on the disease to be treated and associated symptoms, or the stimulation parameters to be applied. In various embodiments, the lead distal portions 350, 351 that contain electrodes are placed to allow bilateral application of electrical signals to the occipital nerve 200 at a level of about C1 to about C2 or at a level in proximity to the base of the skull. The position of the electrode(s) may vary. It will be understood that the electrode need not, and in various embodiments preferably does not, contact the nerve to apply the signal to the nerve. It will be further understood that a signal may be applied to any suitable portion of an occipital nerve, whether at a trunk, branch, or the like. In various embodiments, one or more electrodes are placed between about 1 cm and about 8 cm from the midline to effectively provide an electrical signal to the occipital nerve 200. It will be further understood, that one or the other of the left or right occipital nerve 200 may be stimulated in some embodiments, and both need not be stimulated in all embodiments.

As shown in FIG. 2A, a leads may include paddle shaped distal portions 350, 351 containing electrodes (not labeled). Such paddle shaped leads are often referred to as surgical leads. Examples of surgical leads that may be used or modified to form leads as described herein include Medtronic Inc.'s Resume, SymMix, On-Point, or Specify series of leads. Surgical leads typically contain electrodes that are exposed through one face of the paddle, providing directional stimulation.

As shown in FIG. 2B, the leads may include distal portions 350, 351 that includes electrodes (not labeled) that are generally cylindrically shaped. Such leads are often referred to percutaneous leads. Examples of percutaneous leads that may be used or modified to form leads as described herein include Medtronic Inc.'s Quad Plus, Pisces Quad, Pisces Quad Compact, or 1×8 SubCompact, 1×8 Compact, and 1×8 Standard leads. Such percutaneous leads typically contain ring electrodes that apply an electrical stimulation signal to tissue in all directions around the ring. Accordingly, the amplitude of the signal (and thus the energy required from the signal generator) applied may be greater with percutaneous leads than surgical leads for occipital nerve therapies.

Figure 3:
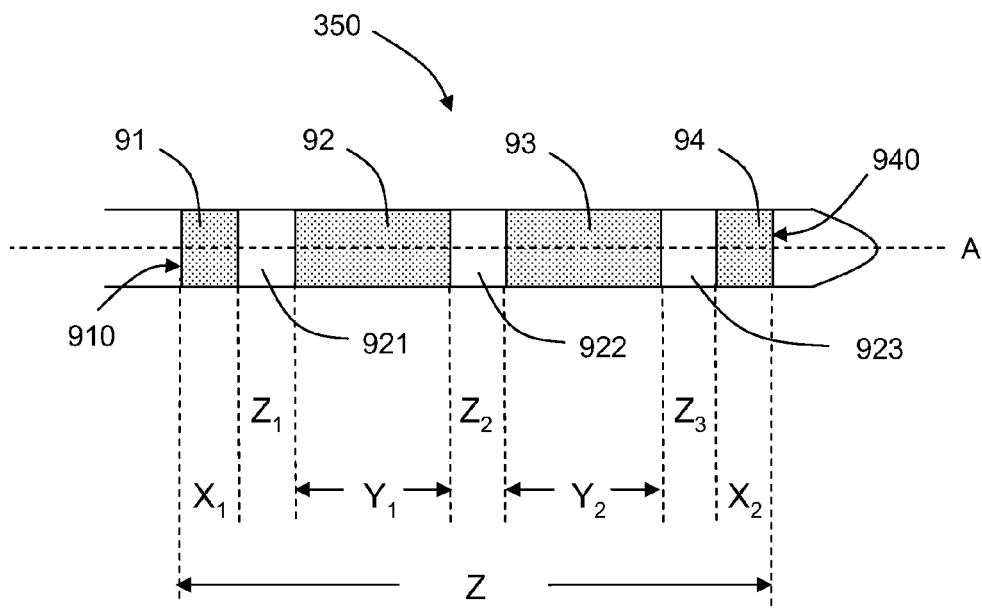
FIG. 3 and FIGS. 4A-D are schematic drawings of distal portions of leads showing some embodiments of electrode arrangements that may be employed in accordance with the teachings presented herein.
Figure 4A:
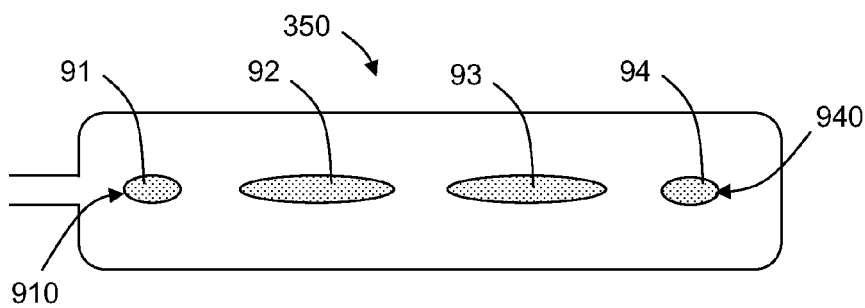
Figure 4B:
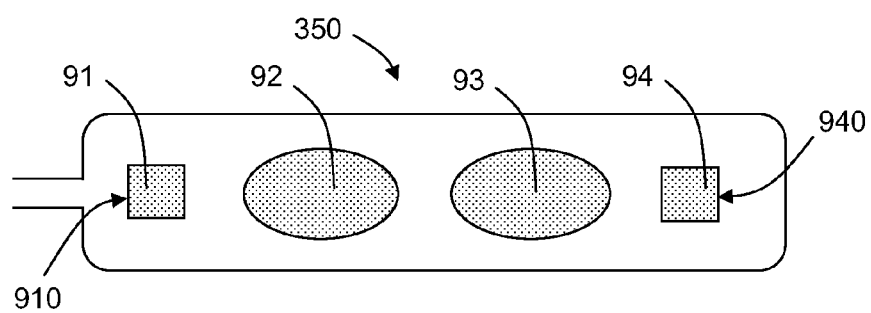
Figure 4C:
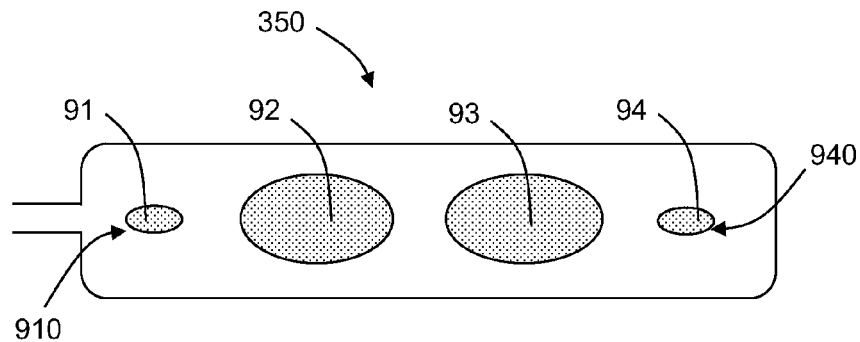
Figure 4D:
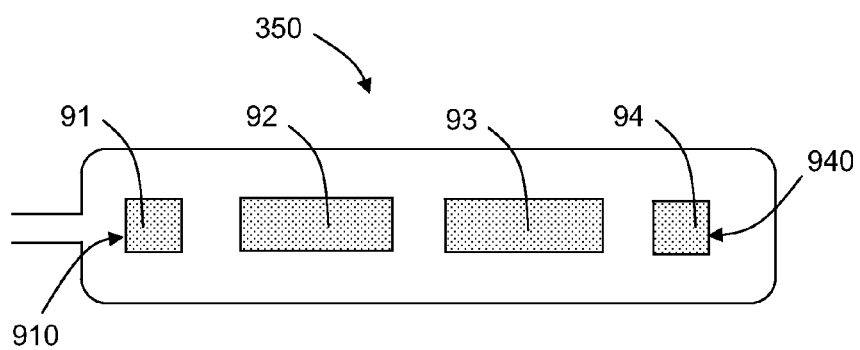

Referring now to FIG. 3, a distal portion 350 of a lead particularly suitable for application of electrical signals to an occipital nerve is shown. The lead has a first electrode 91, a second electrode 92, a third electrode 93, and a fourth electrode 94. The second 92 and third 93 electrodes are located between the first 91 and fourth 94 electrodes. The first electrode 91 is the most proximal electrode, and the fourth electrode 94 is the most distal electrode. The distance (Z) from the proximal end 910 of the first electrode 91 to the distal end 940 of the fourth electrode 94 is between 5 and 8 centimeters; e.g., between 5 and 7 centimeters or between 5.5 and 6.5 centimeters. This distance (Z) is a distance (i) from the midline of a patient's neck or back of the head at a level of about C1 to C2 or at a level in proximity to the base of the skull to (ii) the third occipital nerve, which distance also encompasses the greater and lesser occipital nerves (see, e.g., FIGS. 2A-B). Accordingly, if a lead depicted in FIG. 3 is implanted subcutaneously perpendicular to the midline at a level of about C1 to C2 or at a level in proximity to the base of the skull, at least some of the electrodes 91-94 should be properly positioned to capture a desired occipital nerve in an electric field generated between the appropriately selected electrodes 91-94.

It is desirable for the second electrode 92 or third electrode 93 to be positioned over the desired occipital nerve when implanted. This will allow an electrical field to be generated using the first 91 and second 92 electrodes or the third 93 and fourth 94 electrodes to capture the nerve within the electrical field and deliver the therapeutic electrical signal to the nerve. To increase the chances of the second 92 or third 93 electrode being placed over a desired occipital nerve when implanted, the lengths ($Y_1, Y_2$) of the second 92 and third 93 electrodes occupy the majority of the distance (Z) from the first electrode 91 to the fourth electrode 94. As used herein, the lengths of the electrodes are defined as being in the direction of the axis (A) of the lead body.

In various embodiments, the cumulative lengths ($Y_1+Y_2$) of the second 92 and third 93 electrodes is between 2.5 and 5 times greater than cumulative lengths ($X_1+X_2$) of the first 91 and fourth 94 electrodes.

In some embodiments, the lengths ($X_1, X_2$) of the first 91 and fourth 94 electrodes are each independently between 4 millimeters and 6 millimeters, In some embodiments, the lengths ($X_1, X_2$) of the first 91 and fourth 94 electrodes are the same.

In some embodiments, the lengths ($Y_1, Y_2$) of the second 92 and third 93 electrodes are each independently between 10 millimeters and 25 millimeters; e.g., between 15 and 25 millimeters. In some embodiments, the lengths ($Y_1, Y_2$) of the second 92 and third 93 electrodes are the same.

In various embodiments, the space 921 between the first 91 and second 92 electrodes spans a distance ($Z_1$) between 4 and 6 millimeters; e.g., about 5 millimeters. In some embodiments, the space 922 between the second 92 and third 93 electrodes spans a distance ($Z_2$) between 4 and 6 millimeters; e.g., about 5 millimeters. In many embodiments, the space 923 between the third 93 and fourth 94 electrodes spans a distance ($Z_3$) between 4 and 6 millimeters; e.g., about 5 millimeters. In some embodiments, distance ($Z_1, Z_2, Z_3$) between the first 91 and second 92 electrodes, between the second 92 and third 93 electrodes, and between the third 93 and fourth 94 electrodes is the same.

While the distances ($Z_1, Z_2, Z_3$) between the electrodes may be of any suitable length, it may be desirable to keep the distances small so that relatively large second 92 and third 93 electrodes may occupy most of the distance (Z) between the first 91 and fourth 94 electrodes.

By having the first electrode 91 and the space 921 between the first 91 and second 92 electrodes occupy a distance of about 1 centimeter, the lead may be advanced in a patient until the proximal end 910 of the first electrode 91 just passes (e.g., by 0.5 cm or less) the midline of the patient's neck. This will allow at least a portion of the second electrode 92 to be placed in a location that is likely to be over an occipital nerve. Further, by placing the second 92 and third 93 electrodes close together by giving them a relatively large length ($Y_1$, $Y_2$), the likelihood that the second electrode 92 or the third electrode 93 is over a desired occipital nerve can be maximized.

While there are other ways to maximize the probability that an electrode will be over a nerve or that the nerve will be captured by electrical stimulation, many may have drawbacks relative to the leads described herein. For example, it may be possible to use a lead having more electrodes (e.g., 8 or 16) closely spaced together, but collectively spanning 5 to 8 centimeters, to make it likely that one or more electrodes will be properly positioned for purposes of capturing an occipital nerve. However, there are increased manufacturing costs associated with making an 8 or 16 electrode lead relative to a 4 electrode lead. In addition, the size of a header or connector of an electrical signal generator must be increased to accommodate the additional contacts that are concomitantly associated with the increased number of leads. It is most often desirable to decrease the size of implantable medical devices, rather than to increase their size, due to patient comfort, quality of health factors, and the like. Further the complexity of the components of the electrical signal generator may need to increase as the number of electrodes increases. For theses and other reasons, a lead as depicted in, and described with regard to, FIG. 3 provides several advantages.

Although the lead depicted in FIG. 3 is of a percutaneous-type lead, it will be understood that any type of lead having electrodes arranged as described with regard to FIG. 3 may be used. For example, and referring to FIG. 4, exemplary paddle- or surgical-type leads are shown having electrode arrangements similar to that depicted in FIG. 3.

Distal portions 350 of embodiments of paddle-type leads are shown in FIGS. 4A-D. The distal paddle-shaped portions 350 have a first electrode 91, a second electrode 92, a third electrode 93, and a fourth electrode 94, which can be spaced and sized as described and discussed with regard to FIG. 3 above. As shown in FIGS. 4A-D, the electrodes 91-94 may be of any suitable shape.

Leads as described herein may be made according to well-known lead manufacturing processes and may include well-known materials and parts.

Figure 5:
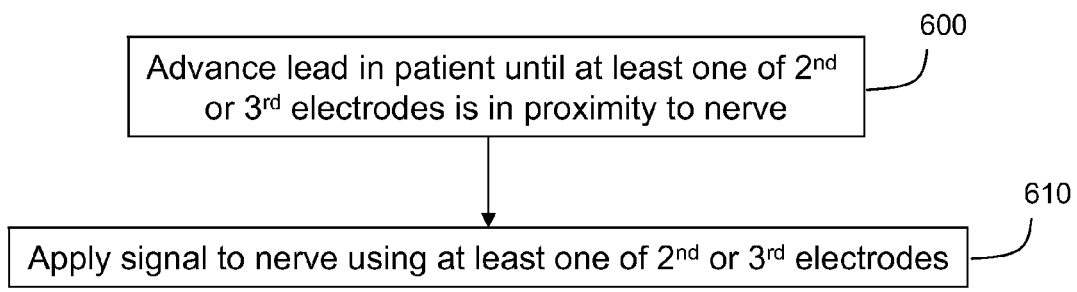
FIGS. 5-6 are flow diagrams illustrating overviews of methods described herein.
Figure 6:
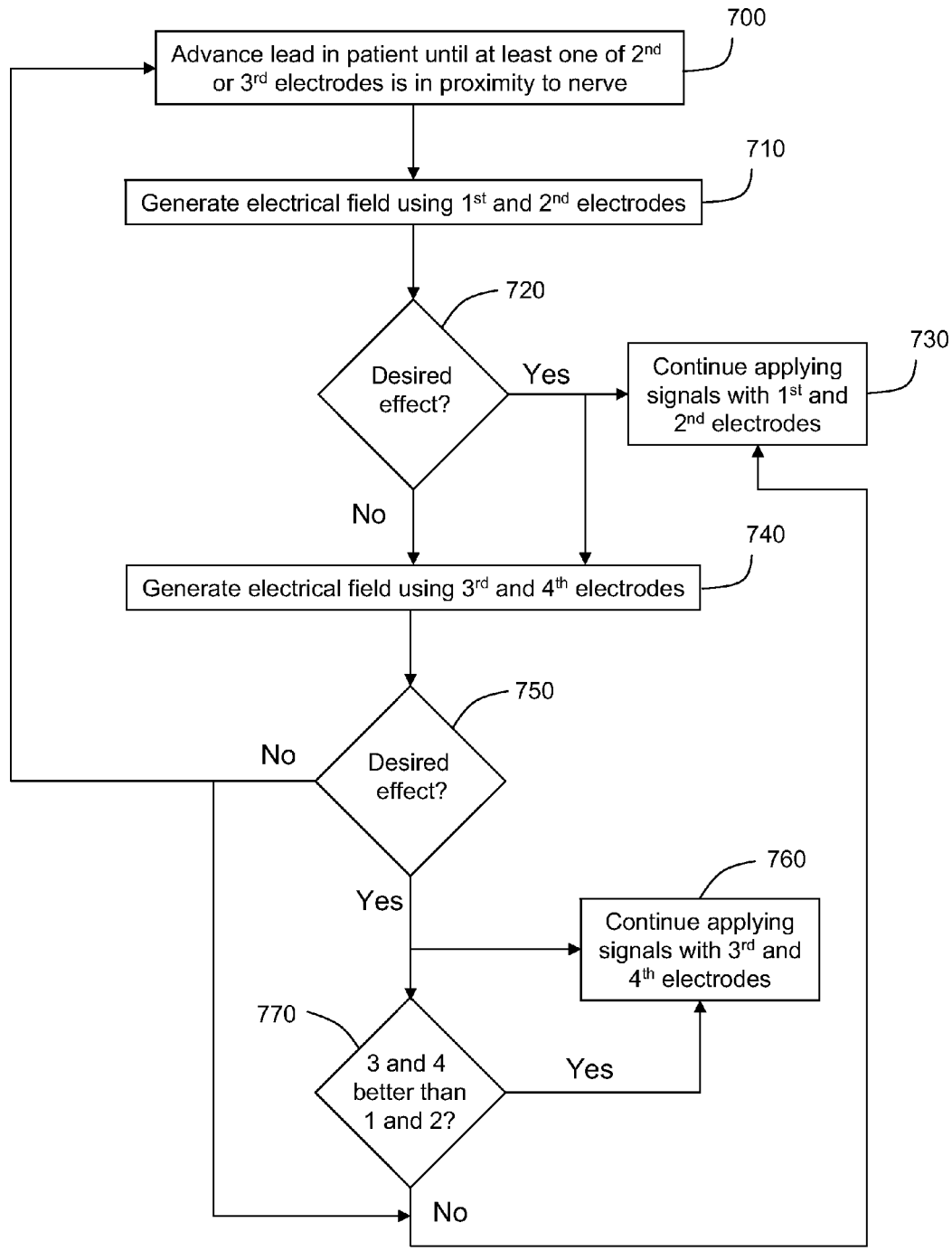

Referring now to FIGS. 5-6, overviews of methods employing the leads described herein are illustrated. With regard to FIG. 5, a method for applying an electrical signal to a nerve includes advancing a distal portion of a lead, having electrodes as described above with regard to FIGS. 3-4, until at least one of the second or third electrodes are in proximity to the nerve (600). As described above, if the nerve is an occipital nerve, the lead may be advanced perpendicular to the midline of the patient's neck, at a level of about C1-C2 or at a level of the base of the skull, until the first electrode just passes the midline. The method further includes applying a signal to the nerve using at least one of the second and third electrodes (610).

With reference to FIG. 6, a method for implanting and selecting electrodes of the lead for use in applying signals to the nerve is depicted. As with the method depicted in FIG. 5, the method depicted in FIG. 6 includes advancing a distal portion of a lead, having electrodes as described above with regard to FIGS. 3-4, until at least one of the second or third electrodes are in proximity to the nerve (700). An electrical field may then be generated using the first and second electrodes (e.g., the first electrode may be set as the cathode and the second electrode may be set as the anode, or vice versa) (710). A determination may then be made as to whether the generated electrical field had a desired effect (720) (e.g., parasthesia in an appropriate area). If the desired effect is achieved, then electrical signals may continue to be applied using the first and second electrodes (730). Optionally, it may be desirable to determine whether better effects can be obtained using the third and fourth electrode.

If a desired effect is not obtained with the use of the first and second electrodes, then an electrical field may then be generated using the third and fourth electrodes (e.g., the third electrode may be set as the cathode and the fourth electrode may be set as the anode, or vice versa) (740). A determination may then be made as to whether the generated electrical field had a desired effect (750). If a desired effect is not achieved using the third and fourth electrodes, the lead may be further advanced, withdrawn, or otherwise moved (700) and the process restarted, if a desired effect was also not achieved by using the first and second electrodes. If a desired effect was achieved by the first and second electrodes but not the third and fourth electrodes, then the electrical signals may be applied by the first and second electrodes (730).

However, if a desired effect is achieved via use of the third and fourth electrodes, then the electrical signals may continue to be applied by the third and fourth electrodes (760). Alternatively, it may be desirable to determine whether the effect achieved with the third and fourth electrodes was better than with the first and second electrodes (770). If the third and fourth electrodes were better than the first and second, then the electrical signals may continue to be applied by the third and fourth electrodes (760). If the third and fourth electrodes were not better than the first and second, then the electrical signals may continue to be applied by the first and second electrodes (730).

The process depicted in FIG. 6 is a fairly simple process relative to, for example, processes that may be employed with leads having 8, 16 or more electrodes. It will, however, be understood that the process depicted in FIG. 6 is but one electrode selection process that may be employed and that combinations of electrodes other than (i) the first and second and (ii) the third and fourth may be used.

Those skilled in the art will recognize that the preferred embodiments may be altered or amended without departing from the true spirit and scope of the disclosure, as defined in the accompanying claims.

What is claimed is:

1. An implantable occipital nerve lead comprising:
a lead body having a proximal portion and a distal portion,
a plurality of contacts located at the proximal portion of the lead body for electrically coupling the lead with an electrical medical device; and
first, second, third and fourth electrodes located at the distal portion of the lead body for transmitting electrical signals to, or receiving electrical signals from, tissue of a patient, wherein each of the first, second, third and fourth electrode is electrically coupled with a discrete contact of the plurality of contacts,
wherein the second and third electrodes are positioned between the first and fourth electrodes,
wherein the first electrode has a proximal end, the fourth electrode has a distal end, and the distance from the proximal end of the first electrode to the distal end of the fourth electrode is between 5 centimeters and 7 centimeters,
wherein the combined length of the second and third electrodes is between 2.5 and 5 times greater than the combined length of the first and fourth electrodes, and
wherein the first and fourth electrodes are the same length and the second and third electrodes are the same length.

2. The lead of claim 1, wherein the lengths of the first and fourth electrodes are between 4 millimeters and 6 millimeters.

3. The lead of claim 1, wherein the lengths of the second and third electrodes are between 10 millimeters and 25 millimeters.

4. The lead of claim 1, wherein the first and fourth electrodes are the same length, wherein the second and third electrodes are the same length, wherein the length of the first and fourth electrodes is between 4 millimeters and 6 millimeters, and wherein the length of the second and third electrodes is between 15 millimeters and 25 millimeters.

5. The lead of claim 4, wherein the first electrode is spaced from the second electrode by a distance of between 4 millimeters and 6 millimeters, the second electrode is spaced from the third electrode by a distance of between 4 millimeters and 6 millimeters, and the third electrode is spaced from the fourth electrode by a distance of between 4 millimeters and 6 millimeters.

6. The lead of claim 5, wherein the distance from the proximal end of the first electrode to the distal end of the fourth electrode is between 5.5 centimeters and 6.5 centimeters.

7. The lead of claim 1, wherein the distance from the proximal end of the first electrode to the distal end of the fourth electrode is between 5.5 centimeters and 6.5 centimeters.

8. An implantable occipital nerve lead comprising:
a lead body;
a first electrode having a proximal end;
a second electrode;
a third electrode; and
a fourth electrode having a distal end,
wherein the first, second, third and fourth electrodes are located at fixed positions along the lead body,
wherein the second and third electrodes are positioned between the first and fourth electrodes,
wherein the distance from the proximal end of the first electrode to the distal end of the fourth electrode is between 5 centimeters and 7 centimeters,
wherein the combined length of the second and third electrodes is between 2.5 and 5 times greater than the combined length of the first and fourth electrodes, and
wherein the first and fourth electrodes are the same length and the second and third electrodes are the same length.

9. The lead of claim 8, wherein the length of the first and fourth electrodes is between 4 millimeters and 6 millimeters, and wherein the length of the second and third electrodes is between 15 millimeters and 25 millimeters.

10. The lead of claim 9, wherein the first electrode is spaced from the second electrode by a distance of between 4 millimeters and 6 millimeters, the second electrode is spaced from the third electrode by a distance of between 4 millimeters and 6 millimeters, and the third electrode is spaced from the fourth electrode by a distance of between 4 millimeters and 6 millimeters.

11. The lead of claim 10, wherein the distance from the proximal end of the first electrode to the distal end of the fourth electrode is between 5.5 centimeters and 6.5 centimeters.

* * * * *